(12) United States Patent
Hsu et al.

(10) Patent No.: US 10,842,413 B2
(45) Date of Patent: Nov. 24, 2020

(54) PIEZOELECTRIC PATCH SENSOR

(71) Applicants: NATIONAL TAIWAN UNIVERSITY, Taipei (TW); NAGASE TAIWAN CO., LTD., Taipei (TW)

(72) Inventors: Yu-Hsiang Hsu, Taipei (TW); Po-Chen Liu, Yunlin County (TW); Chih-Cheng Kuo, Taoyuan (TW); Kuan-Chien Chou, Taipei (TW)

(73) Assignees: NATIONAL TAIWAN UNIVERSITY, Taipei (TW); NAGASE TAIWAN CO., LTD., Taipei (TW)

( * ) Notice: Subject to any disclaimer, the term of this patent is extended or adjusted under 35 U.S.C. 154(b) by 2 days.

(21) Appl. No.: 16/389,405

(22) Filed: Apr. 19, 2019

(65) Prior Publication Data
US 2020/0330002 A1  Oct. 22, 2020

(51) Int. Cl.
*A61B 5/00* (2006.01)
*A61B 5/11* (2006.01)
*A61B 5/0488* (2006.01)

(52) U.S. Cl.
CPC .......... *A61B 5/1107* (2013.01); *A61B 5/0488* (2013.01); *A61B 5/6833* (2013.01);
(Continued)

(58) Field of Classification Search
CPC .................................. A61B 5/00; A61B 5/11
See application file for complete search history.

(56) References Cited

U.S. PATENT DOCUMENTS

| 7,377,133 B2 | 5/2008 | Sandbach et al. |
| 7,712,373 B2 | 5/2010 | Nagle et al. |

(Continued)

OTHER PUBLICATIONS

Meyer et al., "Textile Pressure Sensor for Muscle Activity and Motion Detection", IEEE, International Symposium on Wearable Computers, 2006, pp. 1-4.

(Continued)

*Primary Examiner* — Tran M. Tran
(74) *Attorney, Agent, or Firm* — Allen, Dyer, Doppelt + Gilchrist, P.A.

(57) ABSTRACT

A piezoelectric patch sensor for measuring muscle movement of contraction and extension is disclosed. The sensor is elongated and directly attached to a skin site of a user for the measuring via an interface circuit connected to a host processor. The piezoelectric patch sensor has an adhesive layer with an adhesive bottom surface for firmly attaching to the skin site. An elastic sheet is integrated on top of the adhesive layer. A piezoelectric thread is further integrated on top of the elastic sheet and has a bundle of aligned piezoelectric fibers. The thread is electrically coupled to the interface circuit via a pair of conductive wires, forming a piezoelectric measurement circuitry. Muscle movement under the skin site shrinks or extends the piezoelectric patch sensor in its entirety along the direction of muscle movement due to a corresponding shrinking or extending movement of the skin firmly attached to the adhesive layer. Thus results in the piezoelectric fibers in the measurement circuitry generating a corresponding signal, which is relayed by the interface circuit to the host processor for calculating to derive the muscle movement.

20 Claims, 10 Drawing Sheets

(52) U.S. Cl.
CPC ............... *A61B 2562/0247* (2013.01); *A61B 2562/0261* (2013.01)

(56) References Cited

U.S. PATENT DOCUMENTS

| | | | | |
|---|---|---|---|---|
| 8,961,439 B2* | 2/2015 | Yang | .................... | A61B 5/1038 |
| | | | | 600/595 |
| 9,322,121 B2 | 4/2016 | Dunne et al. | | |
| 9,850,600 B2 | 12/2017 | Gal | | |
| 9,885,621 B2 | 2/2018 | Dunne et al. | | |
| 10,427,293 B2* | 10/2019 | Asbeck | ................. | B25J 9/0006 |
| 10,559,184 B2* | 2/2020 | Harsdorff | ............. | A61B 5/6807 |
| 2017/0029985 A1 | 2/2017 | Tajitsu et al. | | |

OTHER PUBLICATIONS

Yang et al., "Nanofibrous Smart Fabrics from Twisted Yarns of Electrospun Piezopolymer", ACS Appl. Mater. Interfaces, 9, 24220, 2017, pp. 24220-24229.

Baniasadi et al., "High-Performance Coils and Yarns of Polymeric Piezoelectric Nanofibers", ACS Appl. Mater. Interfaces, 7, 2015, pp. 5358-5366.

Huang et al., "A review on polymer nanofibers by electrospinning and their applications in nanocomposites", Elsevier, Composites Science and Technology, Jan. 2003, pp. 2223-2253.

Mandal et al., "Origin of piezoelectricity in an electrospun poly (vinylidene fluoride-trifluoroethylene) nanofiber web-based nanogenerator and nono-pressure sensor", Macromolecular Rapid Communications, Apr. 2011, Abstract Only, pp. 1-2.

Persano et al., High performance piezoelectric devices based on aligned arrays of nanofibers of poly (vinylidenefluoride-co-trifluoroethylene), Nature Communications, 2013, pp. 1-49.

Kaushik et al., "Textile-based electronic components for energy applications: principles, problems, and perspective", Nanomaterials, 2015, pp. 1-40.

Kim et al., "Harvesting electrical energy from carbon nanotube yarn twist", Science 357, Aug. 2017, pp. 1-7.

* cited by examiner

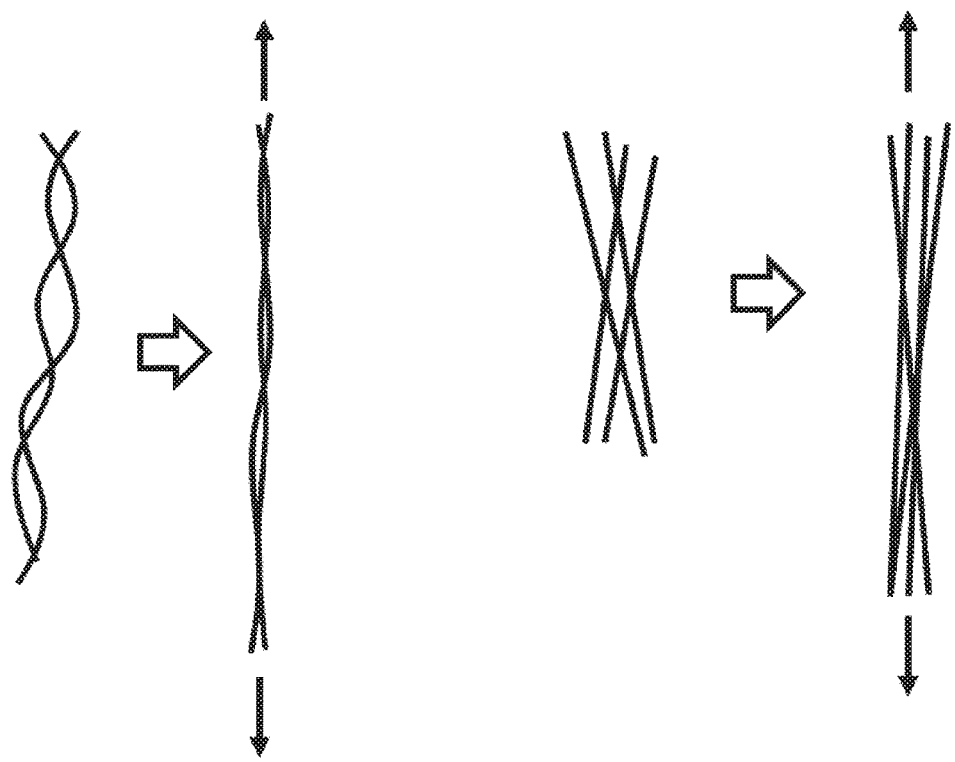
FIG. 6A
FIG. 6B
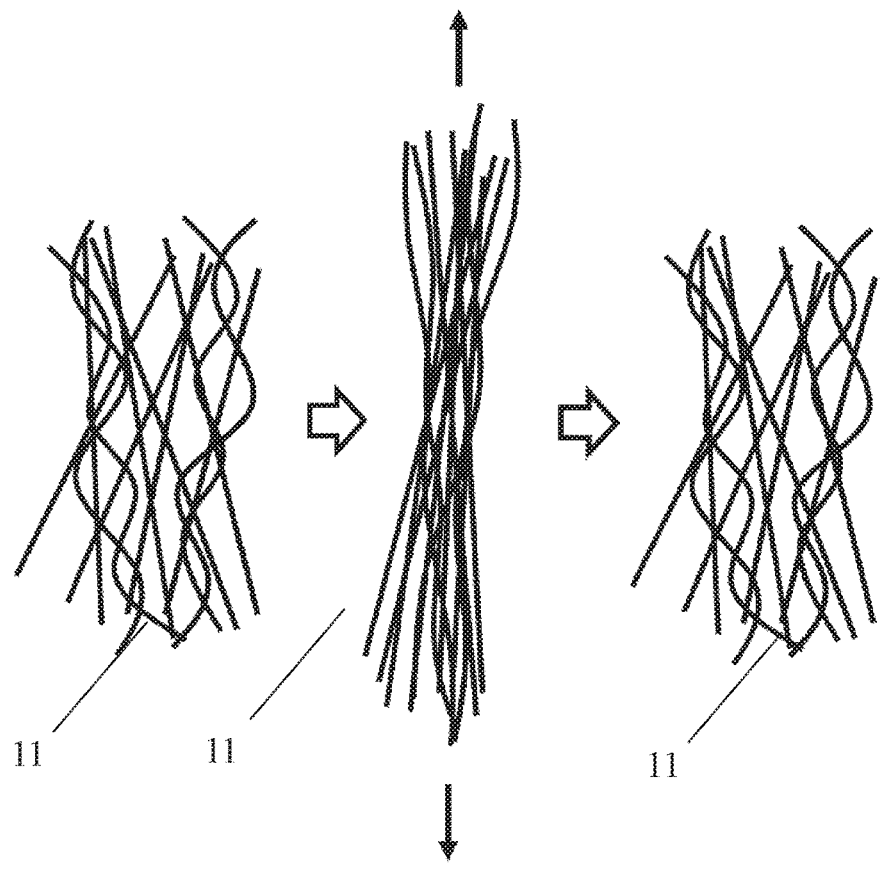
FIG. 6C

PIEZOELECTRIC PATCH SENSOR

FIELD

The present invention relates in general to a piezoelectric patch sensor and, in particular, to the construction thereof. More particularly, the present invention relates to a piezoelectric patch sensor directly attachable to the skin for muscle contraction and extension measurements useful for gesture sensing, athletic training, gaming, and health care, among others.

BACKGROUND

Wearable textile sensor has been used to detect various physiological conditions of a human subject, such as body movement, gesture, touch, heart rate, etc. Two important characteristics are usually required since the major application is to embed the sensing capability into the fabrics. They are stretchability and flexibility.

The concept of fabricating electrically conductive polymer or piezo-resistive material into yarns and stitching or knitting them into a fabric has been reported previously (U.S. Pat. No. 9,322,121 B2, U.S. Pat. No. 9,885,621 B2, U.S. Pat. No. 7,377,133 B2 and U.S. Pat. No. 9,850,600 B2). To increase the range of extensibility, these conductive/piezo-resistive yarns are usually stitched or knitted with different looping techniques into a fabric. Using this type of design, the signal output is usually not linear, leading to low repeatability, and their signal processing may become very complicated when the deformation is large.

On the other hand, the concept of using multi-layered conductive polymer to construct a capacitance sensor also is reported for the measurement of chest movement (U.S. Pat. No. 7,712,373 B3) and muscle activities (J. Meyer, P. Lukowicz, G. Troster, "Textile Pressure Sensor for Muscle Activity and Motion Detection," 2006 IEEE International Symposium on Wearable Computers). The creation of a larger area is required to achieve flexible capacitance for deformation and pressure measurement.

Meanwhile, piezoelectric polymers are also applied in textile sensors. P(VDF-TrFE) yarn is twisted and fabricated into a woven piezoelectric fabric for smart fabric applications (US 2017/0029985 A1, Yang et. Al., "Nanofibrous Smart Fabrics from Twisted Yarns of Electrospun Piezopolymer," 2017 ACS Appl. Mater. Interfaces, 9, 24220). Using a twisted piezoelectric yarn, the range of strain measurement can be very large (M. Baniasadi et. al., "High-Performance Coils and Yarns of Polymeric Piezoelectric Nanofibers," 2015 ACS Appl. Mater. Interfaces, 7). However, due to the twisting structure, the signal-to-strain distribution is highly non-linear and the repeatability for long term use can be an issue.

The main approach of such conventional wearable textile sensors is based on the idea of embedding electrically conductive, piezo-resistive or piezoelectric yarns into a fabric. Such integration usually implies specificity, meaning these methods require high level of processing compatibility to industrial fabrication methods. The fabricated yarns need to have sufficient strength and chemical compatibility to pass the fabrication process of fabrics, and it could be a very complicated process with a considerable cost.

This means that these conventional sensing-capable fabrics are relatively too expensive to be single-use only. They need to be durable for a reasonable cycles of laundering, which itself is the main contribution to high cost.

Also, embedding sensing means in fabrics means the sensing of true contraction and extension movement of a measured muscle must be implemented with limited slip between the sensor-embedded fabric and the skin directly underneath. Even wearing compression sportswear, slip is inevitable, which leads to faulty sensing.

SUMMARY

It is an object of the present invention to provide a piezoelectric patch sensor that can be made inexpensively for single use in muscle movement measurement.

It is also an object of the present invention to provide a piezoelectric patch sensor that can be directly attached to the skin for improved muscle movement measurement via uni-directional sensor aligned along, transverse or in an oblique angle with respect to the direction of muscle movement.

It is another object of the present invention to provide a piezoelectric patch sensor that can also be attached to a fabric of a compression garment for indirect muscle movement measurement.

It is yet another object of the present invention to provide a piezoelectric patch sensor that can relay measurement signal easily to back-end host processor for derivation of numerical measurement of muscle movement.

In order to achieve the above and other objects, the present invention provides a piezoelectric patch sensor for measuring muscle movement of contraction and extension is disclosed. The sensor is elongated and directly attached to a skin site of a user for the measuring via an interface circuit connected to a host processor. The piezoelectric patch sensor has an adhesive layer with an adhesive bottom surface for firmly attaching to the skin site. An elastic sheet is integrated on top of the adhesive layer. A piezoelectric thread is further integrated on top of the elastic sheet and has a bundle of aligned piezoelectric fibers. The thread is electrically coupled to the interface circuit via a pair of conductive wires, forming a piezoelectric measurement circuitry. Muscle movement under the skin site shrinks or extends the piezoelectric patch sensor in its entirety along the direction of muscle movement due to a corresponding shrinking or extending movement of the skin firmly attached to the adhesive layer. Thus results in the piezoelectric fibers in the measurement circuitry generating a corresponding signal, which is relayed by the interface circuit to the host processor for calculating to derive the muscle movement.

In an implementation of the piezoelectric patch sensor a second elastic sheet is further integrated on top of the piezoelectric thread, and the piezoelectric thread is firmly embedded between the two elastic sheets.

In an implementation of the piezoelectric patch sensor the interface circuit is integrated on the piezoelectric patch sensor.

In an implementation of the piezoelectric patch sensor the interface is connect to the host processor wirelessly.

In an implementation of the piezoelectric patch sensor the host processor is a portable device.

In an implementation of the piezoelectric patch sensor the piezoelectric fibers are fibers of piezoelectric polymer.

In an implementation of the piezoelectric patch sensor the piezoelectric polymer is selected from among polyvinylidene fluoride (PVDF) polymer and poly(vinylidene fluoride-trifluoroethylene) [P(VDF-TrFE)]copolymer.

In an implementation of the piezoelectric patch sensor the piezoelectric thread is thermally bound between the two elastic sheets.

In an implementation of the piezoelectric patch sensor the two elastic sheets have an adhesive layer on the surface facing the piezoelectric thread for bonding the piezoelectric thread therebetween.

In an implementation of the piezoelectric patch sensor the elastic sheet has a thickness of between 0.01 mm to 1 mm, allowing the sheet to measure small deformations and withstand large deformations, where the range of strain can be as low as 1% or as high as 80%.

In an implementation of the piezoelectric patch sensor the adhesive layer has a thickness of between 0.01 mm to 1 mm.

In an implementation of the piezoelectric patch sensor the two conductive wires are connected to electrodes at two ends of the piezoelectric thread such that the condition of piezoelectric constant $d_{33}$ is aligned with the longitudinal direction of the piezoelectric thread.

In an implementation of the piezoelectric patch sensor one of the two conductive wires is connected to top of the piezoelectric thread and the other is connected to the bottom of the piezoelectric thread such that the condition of piezoelectric constant $d_{31}$ is aligned with the longitudinal direction of the piezoelectric thread.

In an implementation of the piezoelectric patch sensor the two conductive wires are connected to the piezoelectric thread using conductive glue.

In an implementation of the piezoelectric patch sensor the two conductive wires connected to the piezoelectric thread are electrically conductive paths formed using printed conductive ink selected from the group consisting of silver, graphene, Carbone nanoparticles, Carbone nanotube, and PEDOT [poly(3,4-ethylenedioxythiophene) polystyrene sulfonate.

In an implementation of the piezoelectric patch sensor the two conductive wires are deformable to withstand the deformation of muscle movement without exceeding mechanical constrain.

In an implementation of the piezoelectric patch sensor the interface circuit has a first unit connecting directly to the piezoelectric thread for converting the piezoelectric signal into a physical quantity; a second unit amplifying and filtering the piezoelectric signal; and a third unit recording and transmitting the piezoelectric signal to the host processor.

In an implementation of the piezoelectric patch sensor the attachment to the skin site is transversely or in an oblique angle with respect to the direction of muscle movement.

In an implementation of the piezoelectric patch sensor an additional grounded conductive layer shields the piezoelectric thread against electromagnetic interference.

BRIEF DESCRIPTION OF THE DRAWINGS

FIG. 6A shows the first type of aligned piezoelectric fibers that can sustain and respond to applied mechanical stretching with higher linearity and repeatability.

FIG. 6B shows the second type of aligned piezoelectric fibers that can sustain and respond to applied mechanical stretching with higher linearity and repeatability.

FIG. 6C shows general structure of the aligned piezoelectric fibers for the piezoelectric thread. It is a combination of the first and the second type of aligned piezoelectric fibers shown in FIGS. 6B and 6C.

DETAILED DESCRIPTION

Figure 1A:
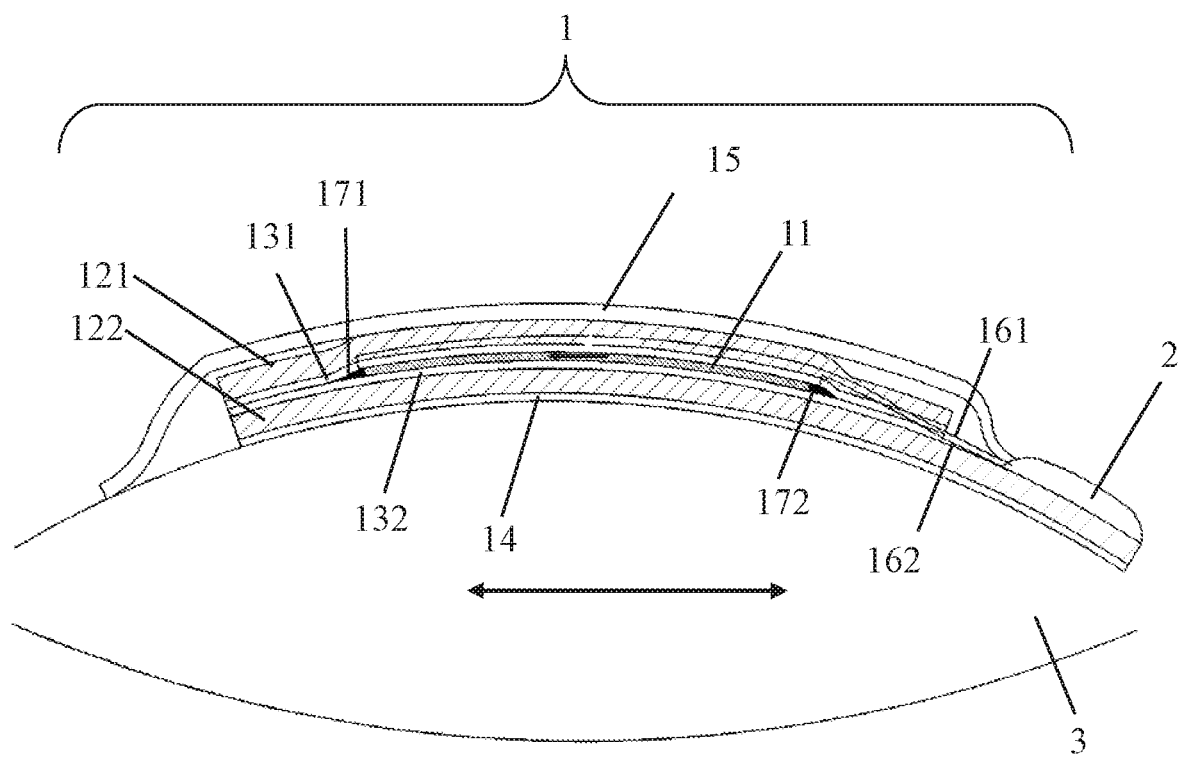
FIGS. 1A and 1B are schematic in cross section of a piezoelectric patch sensor of the present invention as attached to the skin over a muscle, with and without the use of bonding layers respectively.

FIG. 1A is an illustration of a piezoelectric patch sensor 1 and its interface circuit 2 attached on the skin of a human muscle 3 according to an embodiment of the present invention. The measuring direction and the poling direction (black arrow) of the piezoelectric thread 11 is aligned with the contraction direction of the muscle (black line with two arrows) to have a unidirectional measurement of the muscle contractions. The piezoelectric thread is sealed between two elastic sheet 121 and 122 by using two bonding layer 131 and 132. The two ends of the piezoelectric thread are connected to two conductive wires 161 and 162 by using conductive glue or conductive ink 171 and 172 to serve as the two electrodes for the piezoelectric thread. These two conductive wires, glue or ink are sealed between the two elastic sheets.

The interface circuit is also bounded on the surface of the bottom elastic sheet 122. The bottom elastic sheet is adhered to the skin of the muscle 3 by the adhesive layer 14. Finally, a conductive layer 15 for EMI shielding covers the overall area of the piezoelectric patch sensor. The conductive layer 15 is optional. It is to reduce environmental noise such as a gymnasium or indoor environment.

The thickness of the elastic sheet 121 and 122, the bounding layers 131 and 132, and the adhesive layer 14 are thin enough so that the deformation of the muscle contraction can directly be, literally, passed on to the piezoelectric thread 11. The conductive wires 161 and 162 also have a low elasticity and are very flexible so that it can follow muscle contraction without breaking down signal conductions to the interface circuit 2. These two conductive wires can also be made of conductive ink that printed on the elastic sheets for connection.

In an embodiment of the piezoelectric patch sensor, the elastic sheet has a very low viscoelastic property with a very small hysteretic property. Its elasticity is lower than muscle and skin, and it can compliantly following the deformation of muscle without or with a minimal induction of mechanical constraint to the muscle contractions. It is responsible of the elastic deformation of the piezoelectric patch sensor during elongation and contraction of attached muscle, and its deformation drive the piezoelectric thread to elongate and contract with sufficient linearity and fidelity output.

In an embodiment of the piezoelectric patch sensor, the elastic sheet can withstand and measure small and/or large deformations, where the range of strain can be as low as 1% or as high as 80%. For example, thermoplastic polyurethane, silicone rubber, elastomer, etc.

In an embodiment of the piezoelectric patch sensor the elastic sheet allows the elongated body of the piezoelectric patch sensor to be stretched when deploying to the skin over a muscle. This pre-stretching is to provide an initial tension in the piezoelectric thread.

In an embodiment of the piezoelectric patch sensor the side of the elastic sheets that facing to the piezoelectric thread has a bonding layer made of an adhesive or coated with a thermal adhesive layer for bounding piezoelectric thread onto or between the elastic sheets.

In an embodiment of the piezoelectric patch sensor the elastic sheets can be soften to press piezoelectric thread into its body.

In an embodiment of the piezoelectric patch sensor the adhesive layer that attaches to human body is compliant to the contraction of muscle. It has a very low hysteretic property and the thickness is thin enough for transmit muscle contraction to the elastic sheet and the piezoelectric thread.

In an embodiment of the piezoelectric patch sensor that the body of the piezoelectric patch sensor is covered by another layer of grounded conductive layer for EMI (electromagnetic interference) shielding. This conductive layer can be a metal mesh or an elastic sheet or fabric that coated or printed with conductive metal or conductive polymer. This layer can be relatively stiff and covers the piezoelectric patch sensor, it allows the piezoelectric patch sensor to deform inside its cavity without additional constrain.

In an embodiment of the piezoelectric patch sensor that the EMI shielding can be a conductive layer made of a conductive polymer or a fabric made of conductive threads or a fabric printed with a conductive ink. This grounded conductive layer can be a compliant elastic sheet that bonds with the piezoelectric patch sensor and follows the deformation without induction of mechanical strain.

In an embodiment of the piezoelectric patch sensor that the EMI shielding is a conductive ink printed on the top surface of the top elastic sheet 121. It can also be a conductive metal coated on the top surface of the top elastic sheet 121.

Figure 1B:
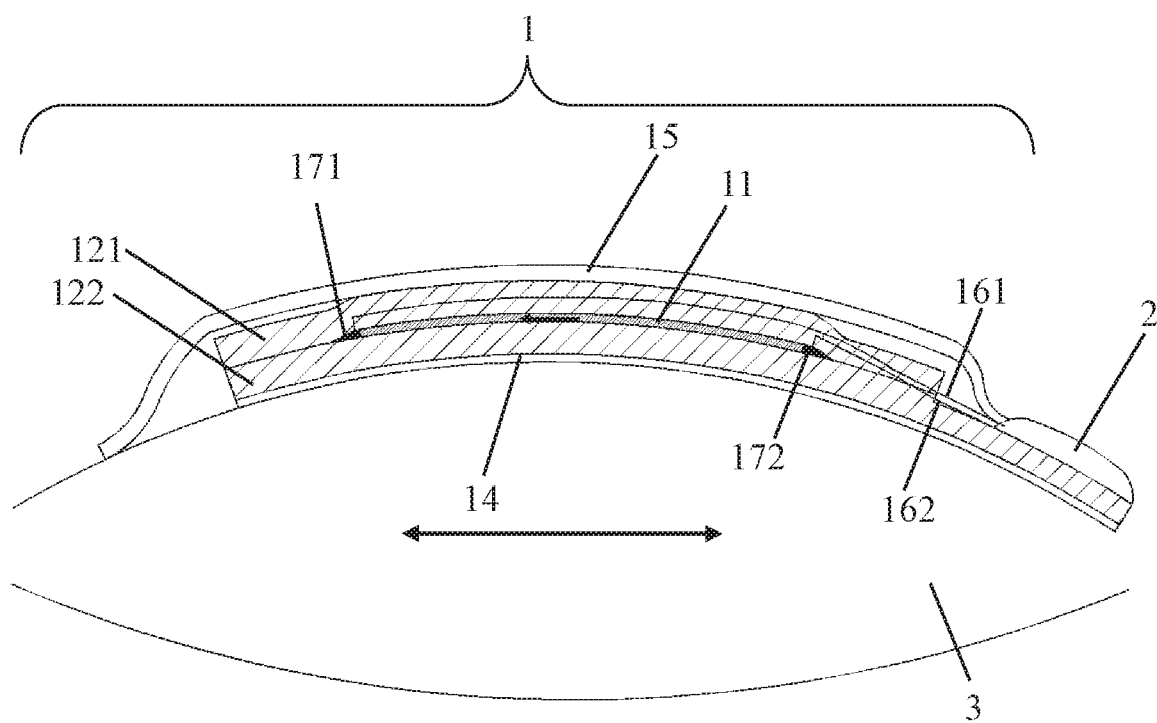

FIG. 1B is an illustration of another embodiment of a piezoelectric patch sensor. The difference to the design shown in FIG. 1A is the piezoelectric thread 11 is sealed between the elastic sheet 121 and 122. This can be done by making the piezoelectric thread to be thermally sealed between the elastic sheets. Thus, the bonding layer 131 and 132 are not needed.

Figure 2:
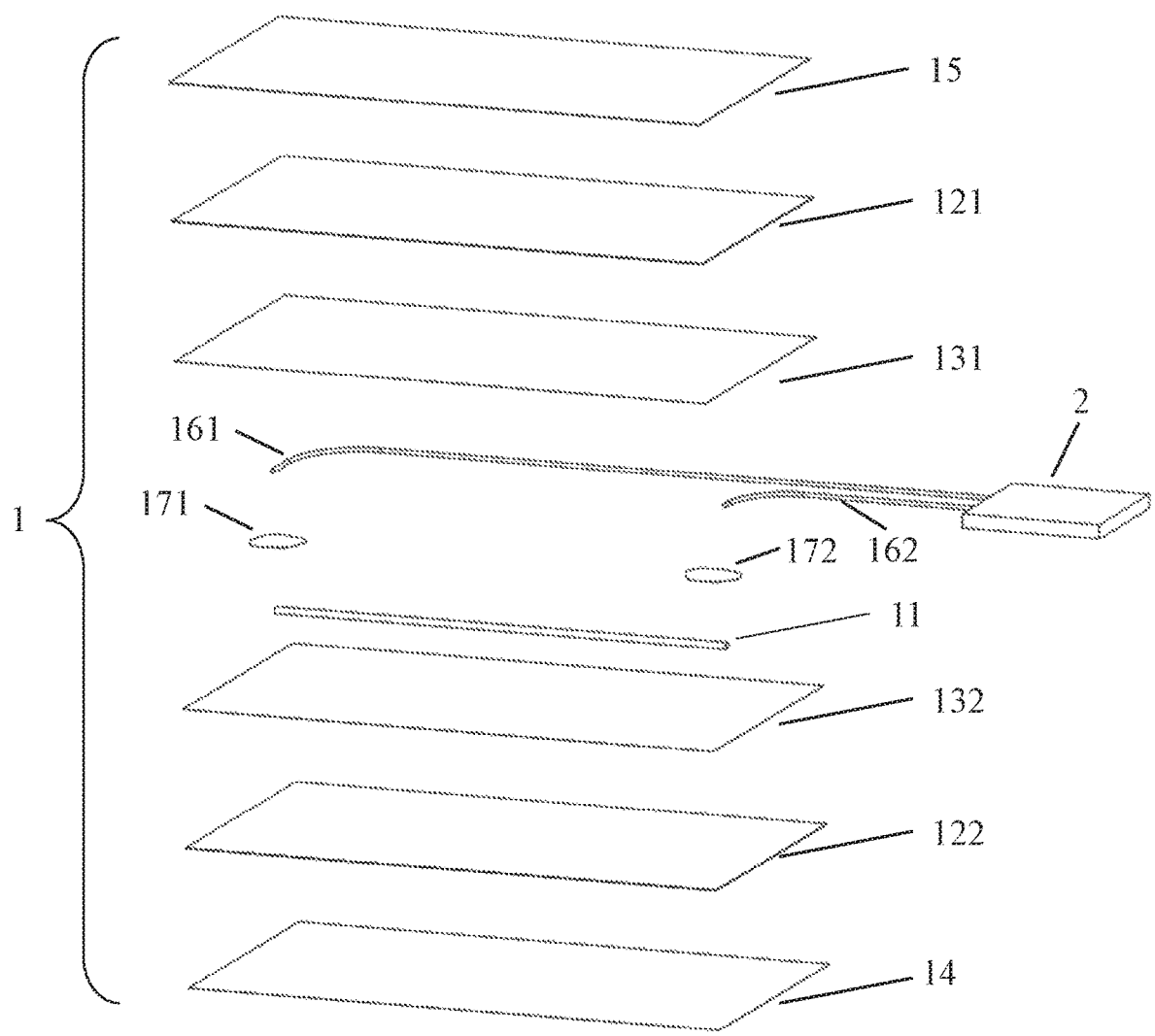
FIG. 2 is an exploded view showing the construction of the piezoelectric patch sensor of FIG. 1A.

FIG. 2 schematically illustrates structural layered construction of a piezoelectric patch sensor according the present invention of FIG. 1A. The piezoelectric patch sensor 1 includes the piezoelectric thread 11, two elastic sheets 121 and 122, two bonding layer 131 and 132, one adhesive layer 14, a conductive layer 15 for EMI shielding, two conductive wire 161 and 162, two conductive glue or ink 171 and 172. The piezoelectric patch sensor is connect to an interface circuit 2.

Figure 3A:
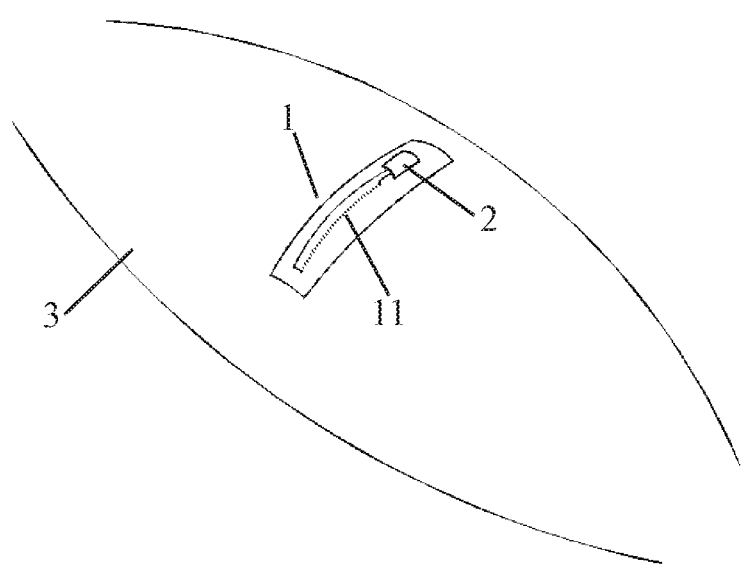
FIGS. 3A and 3B schematically depict the attachment of a piezoelectric patch sensor of the present invention to the skin aligned respectively to a perpendicular and a parallel direction with respect to muscle contraction and extension, each with a dedicated interface circuit for the sensor.
Figure 3B:
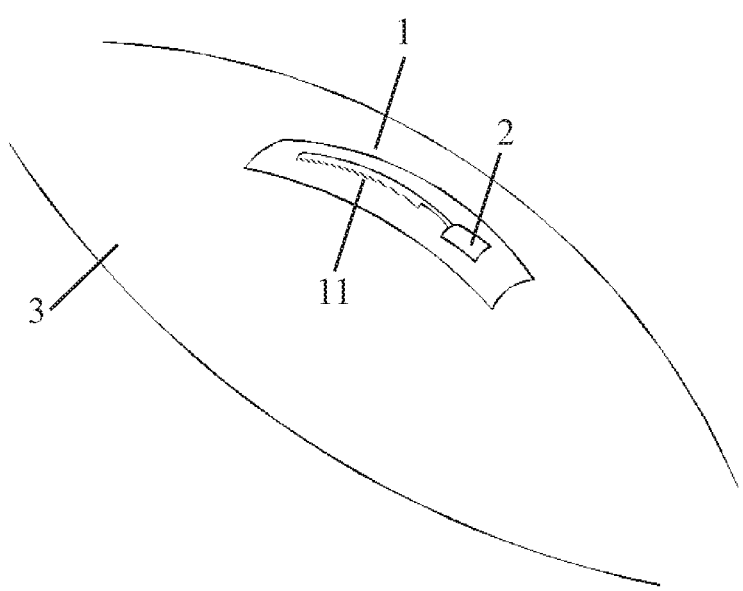

FIGS. 3A and 3B are, respectively, a piezoelectric patch sensor attached on the skin of a muscle in parallel and perpendicular with respect to the direction of muscle contraction. The interface circuit 2 is placed on the same elastic sheet of the piezoelectric thread. The configuration of the piezoelectric patch sensor shown in FIG. 3A can measure the enlargement and reduction of muscle circumference during contractions. On the other hand, the configuration of the piezoelectric patch sensor shown in FIG. 3B is to measure the elongation and shortening of the muscle during contractions.

Figure 4A:
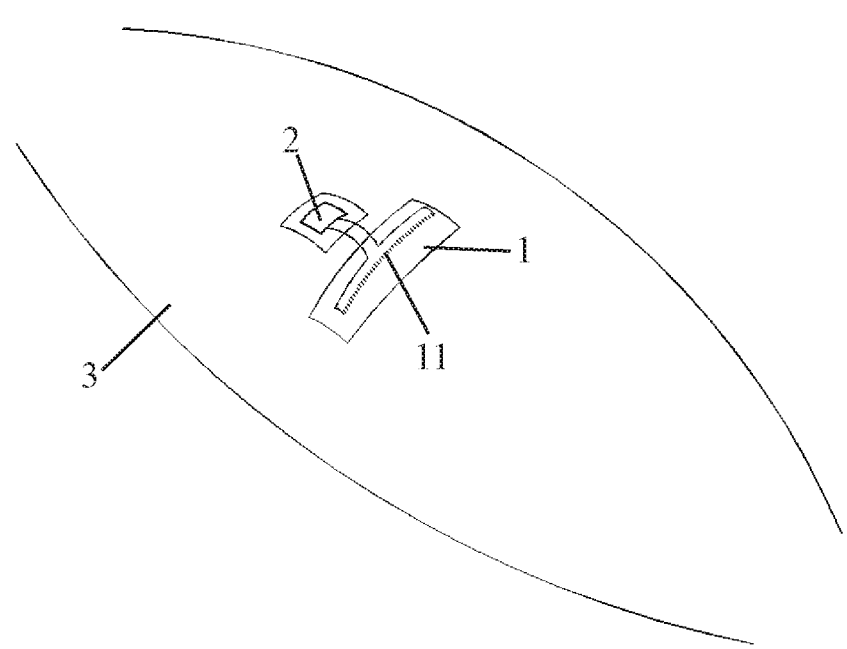
FIGS. 4A and 4B show the same sensor deployment as in FIGS. 3A and 3B but with non-dedicated, reusable interface circuit.
Figure 4B:
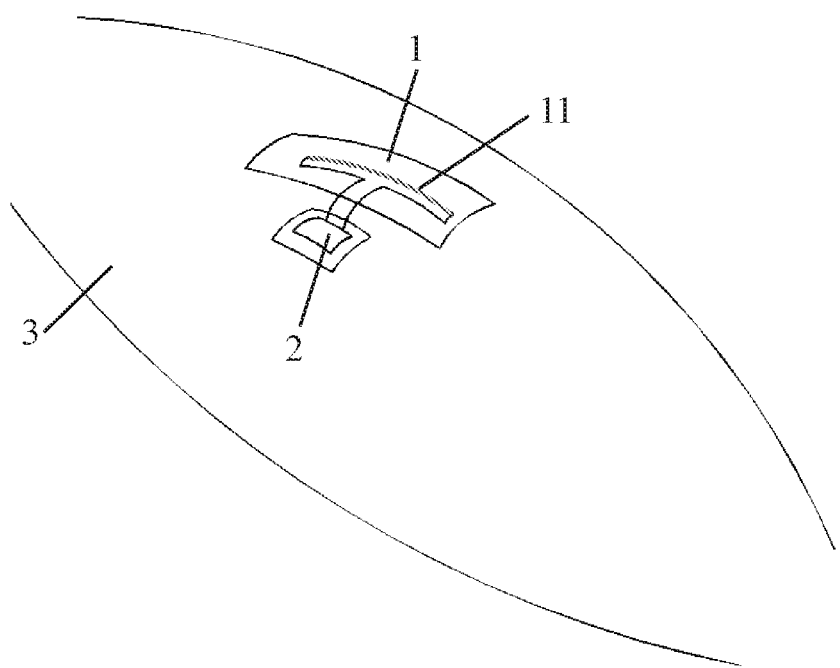

FIGS. 4A and 4B are, respectively, a piezoelectric patch sensor attached on the skin of a muscle in parallel and perpendicular with respect to the direction of muscle contraction. The difference to the design shown in FIGS. 3A and 3B is the interface circuit. It is a separated unit that attached on the skin of the muscle. This design is for reusing the interface circuit and the piezoelectric patch sensor can be disposable.

Figure 5:
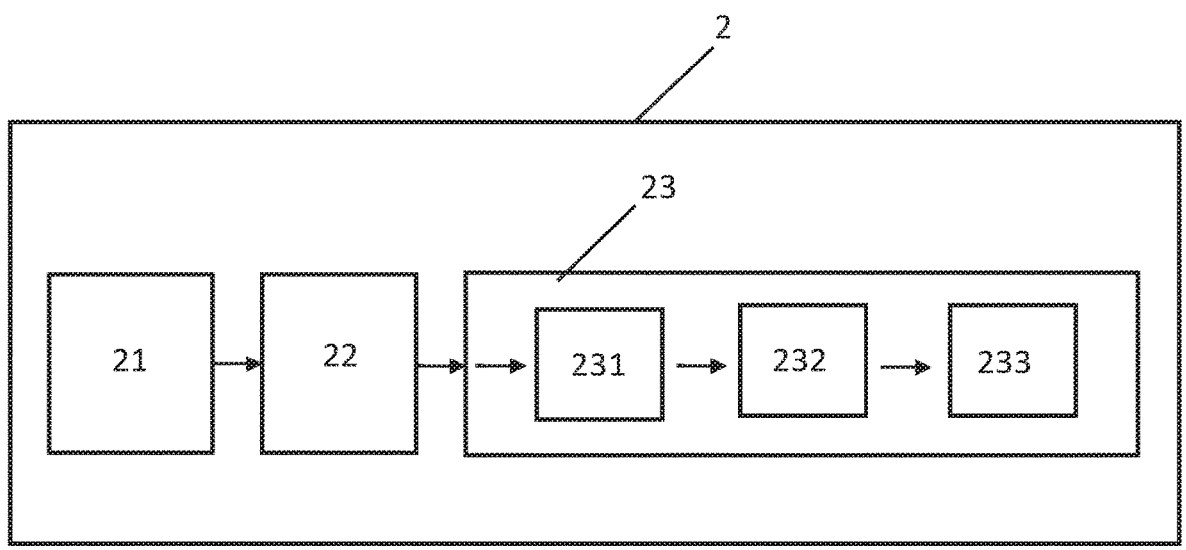
FIG. 5 is a block diagram of the interface circuit.

FIG. 5 is an illustration of the components of the interface circuit 2 and the components of its remote computing unit. The interface circuit 2 includes 3 subunits. The first component 21 directly connects with the piezoelectric thread 11 with the two conductive wires 161 and 162. It can be a charge amplifier to convent piezoelectric signal into an electrical signal that is proportional to the strain deformation of the muscle contractions. It also can be a current amplifier that convert to an electrical signal that is proportional to the strain rate of the muscle contractions. The second component is amplification and filtering unit that amplifies detected signal form 21 and also filters out high frequency noise. The third component is a data recording and transmission unit 23. The unit 23 contains an ADC (analog-to-Digital converter) 231 and a memory to store data 232 and has a transmitting circuit 233 to wirelessly transmit signal to a remote receiver of a computing unit. The computing unit is to perform quantitative analysis. The analyzed result is displayed to user or doctor for personalized health training, body training, or diagnostics.

FIGS. 6A and 6B shows two types of aligned piezoelectric fibers that can sustain mechanical stretching deformation. The first type shown in FIG. 6A has a wavy structures, and it can be stretched to lengthen and provide piezoelectric sensing. The second type shown in FIG. 6B is the fibers have a small skew angle with respect to the direction of force application. These fibers can be straightened during the force application process. FIG. 6C shows the general structure of the piezoelectric thread constructed by these two types of piezoelectric fibers. It can be straightened by a tensile force and return to its original state after releasing of the mechanical force. Then, the mechanical deformation can be detected by the piezoelectric effect.

Figure 7:
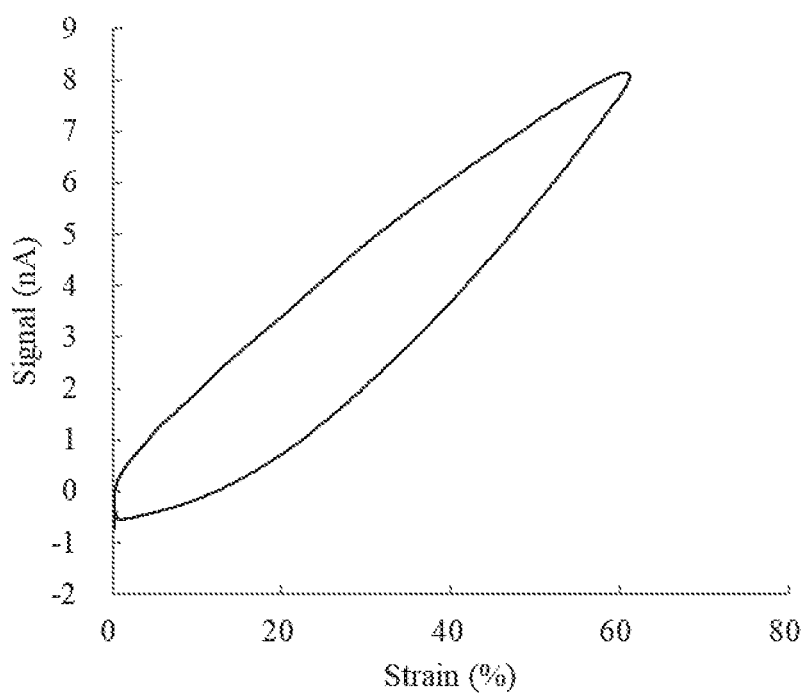
FIG. 7 shows the hysteretic looping characteristic of the strain-induced signal output of a piezoelectric thread used in a sensor of the present invention.

FIG. 7 shows the hysteretic loop of an example of the piezoelectric thread uses in the piezoelectric patch sensor. The piezoelectric thread is made of an electrospun P(VDF-TrFE) fiber bundle. This piezoelectric fiber bundle is firstly aligned by using a cyclic stretching process for 2.5 hours followed by poling processes. Then, this piezoelectric is sandwiched between two elastic sheets to construct the core of the piezoelectric patch sensor. The hysteretic loop shows that the piezoelectric patch sensor can be applied to the large contraction profile of muscles. Furthermore, it has a low level of nonlinearity and can easily be computed for delivering measured strain signal.

Figure 8A:
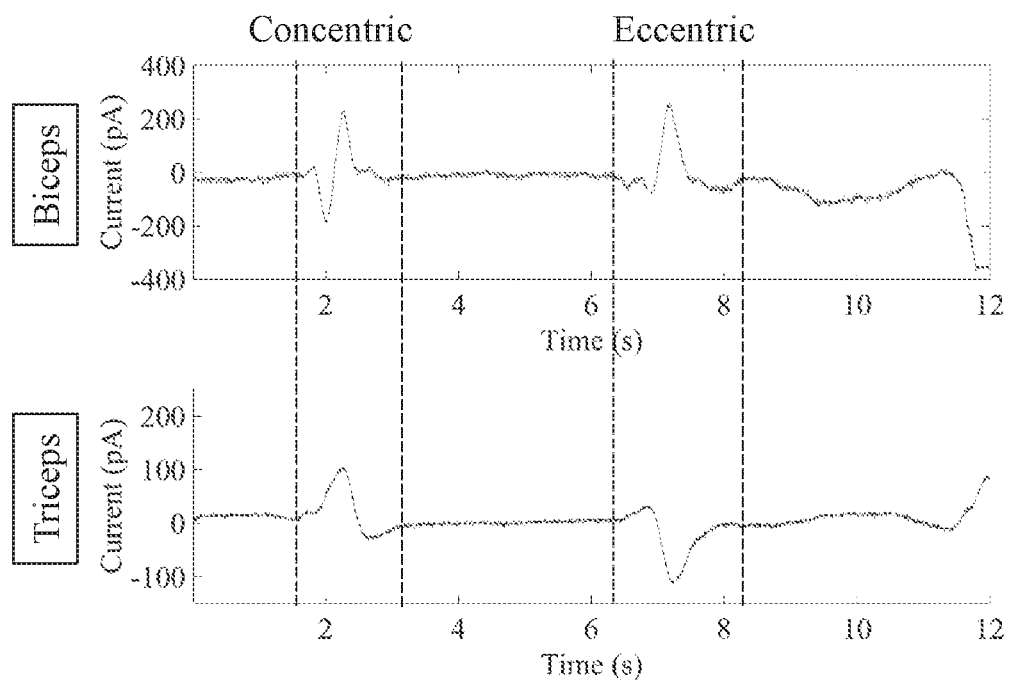
FIG. 8A shows measured concentric and eccentric contraction profiles biceps (top) and triceps (bottom) using a sensor of the present invention in the sensing configuration of FIG. 3A.

FIG. 8A shows an example of the present invention that uses two piezoelectric patch sensors to measure biceps and triceps contractions. The configuration shown in FIG. 3A is used. The concentric and eccentric contraction of biceps and triceps can be measured and monitored simultaneously. Furthermore, the output current of the two piezoelectric patch sensor can clearly monitor the enlargement and reduction of the circumference of the biceps and the triceps during concentric contraction, and vice versa.

Figure 8B:
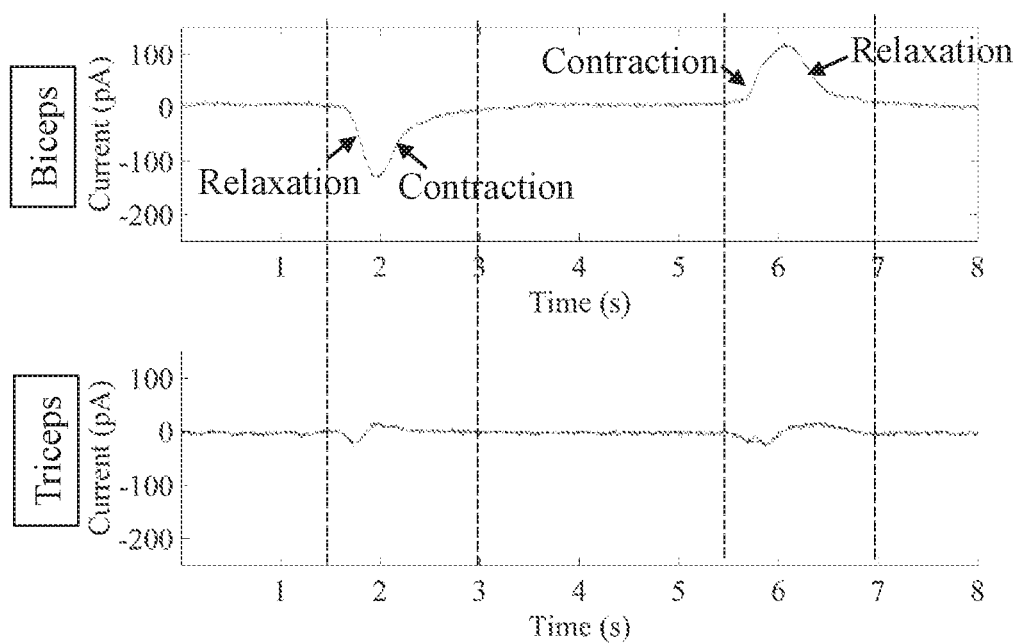
FIG. 8B shows measured contraction and relaxation process of isometric concentric of biceps using a sensor of the present invention in the sensing configuration of FIG. 3A.

FIG. 8B shows another example of the present invention that has identical setup as FIG. 8A. It shows the simultaneous measurement result of isometric contractions for both biceps and triceps. Different contraction profile of the circumference enlargement and relaxation can be distinguished.

Figure 9:
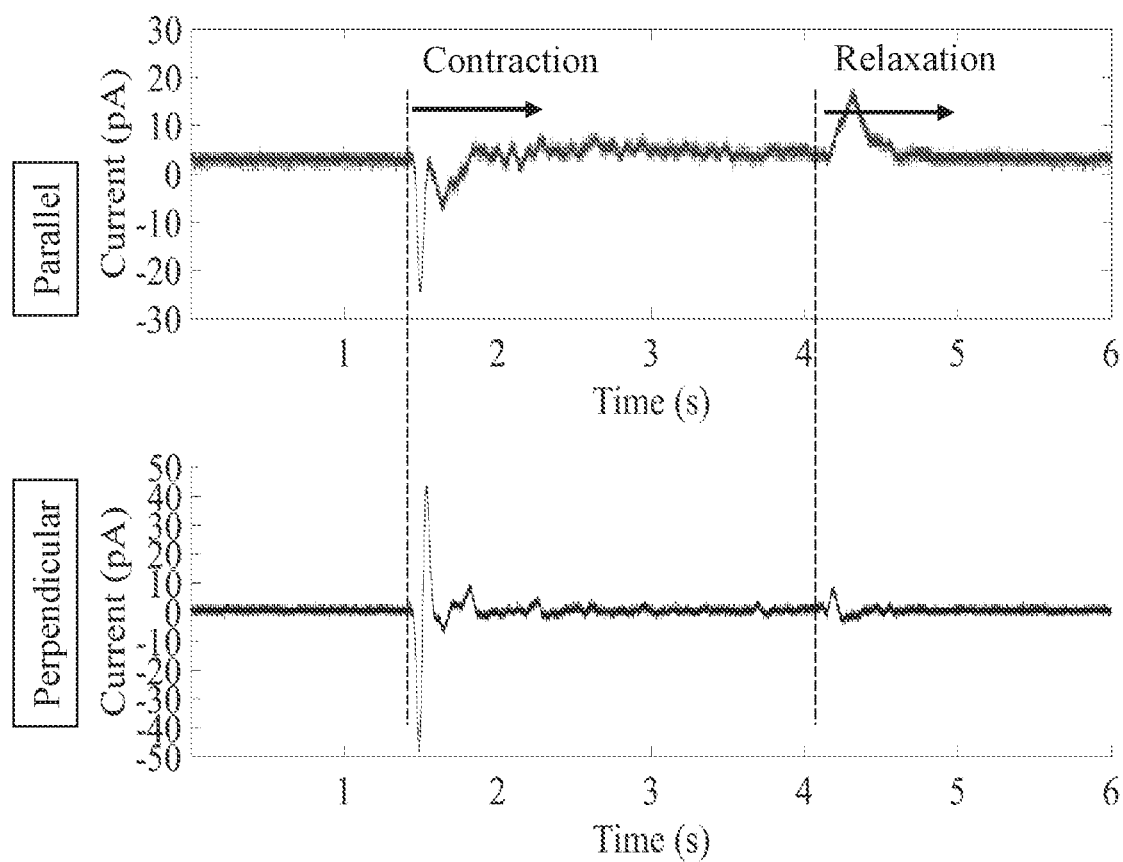
FIG. 9 shows isometric contraction and relaxation of biceps measured by sensors of the present invention in the sensing configuration of FIGS. 3A (top) and 3B (bottom).

In yet another example of the present invention, FIG. 9 shows measured isometric contraction and relaxation of biceps by using two piezoelectric patch sensors. One piezoelectric patch is placed in parallel with direction of muscle contraction as shown in FIG. 3A. The measured signal is shown on the top of FIG. 9. The other is placed perpendicularly as shown in FIG. 3B, and its signal is shown on the bottom of FIG. 9. It clearly demonstrates that the piezoelectric patch sensor can clearly measure the enlargement of the biceps during contraction, and it also can measure the shortening of the biceps length during contraction. Furthermore, the relaxation profiles can also be monitored.

Figure 10:
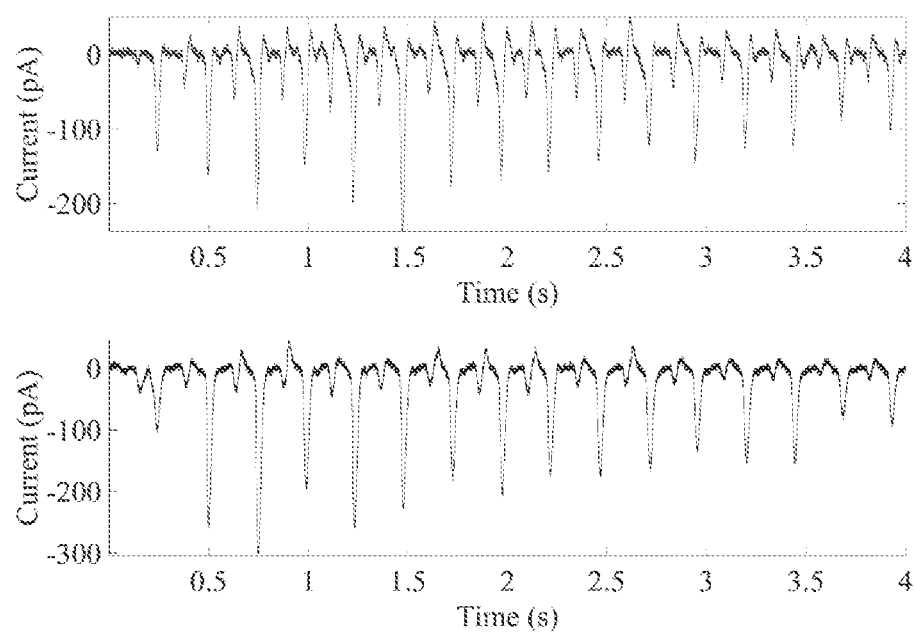
FIG. 10 shows the exercising characteristic profiles of a soleus muscle on one lower leg measured by two sensors of the present invention each deployed to one side of the muscle using the sensing configurations of FIG. 3A.

In still another example of the present invention, FIG. 10 shows the measured profiles of a soleus muscle on one lower leg by attaching two piezoelectric patch sensors on two sides of the soleus muscle. The configuration of these two piezoelectric patch sensors is the same with FIG. 3A. The jumping movement can be measured and it shows a good synchronization of these two piezoelectric patch sensors.

That what is claimed is:

1. A piezoelectric patch sensor for measuring muscle movement of contraction and extension, the sensor being elongated and directly attached to a skin site of a user for the measuring via an interface circuit connected to a host processor, the piezoelectric patch sensor comprising:
   a) an adhesive layer having an adhesive bottom surface for firmly attaching to the skin site;
   b) an elastic sheet integrated on top of the adhesive layer;
   c) a piezoelectric thread integrated on top of the elastic sheet and comprising a bundle of aligned piezoelectric fibers, the thread being electrically coupled to the interface circuit via a pair of conductive wires, forming a piezoelectric measurement circuitry; wherein
   muscle movement under the skin site shrinks or extends the piezoelectric patch sensor in entirety along the direction of muscle movement due to a corresponding shrinking or extending movement of the skin firmly attached to the adhesive layer, resulting in the piezoelectric fibers in the measurement circuitry generating a corresponding signal, which is relayed by the interface circuit to the host processor for calculating to derive the muscle movement.

2. The piezoelectric patch sensor of claim 1 wherein a second elastic sheet is further integrated on top of the piezoelectric thread, and the piezoelectric thread is firmly embedded between the two elastic sheets.

3. The piezoelectric patch sensor of claim 1 wherein the interface circuit is integrated on the piezoelectric patch sensor.

4. The piezoelectric patch sensor of claim 3 wherein the interface is connect to the host processor wirelessly.

5. The piezoelectric patch sensor of claim 1 wherein the host processor is a portable device.

6. The piezoelectric patch sensor of claim 1 wherein the piezoelectric fibers are fibers of piezoelectric polymer.

7. The piezoelectric patch sensor of claim 6 where the piezoelectric polymer is selected from a group consisting of polyvinylidene fluoride (PVDF) polymer and poly(vinylidene fluoride-trifluoroethylene) [P(VDF-TrFE)] copolymer.

8. The piezoelectric patch sensor of claim 2 wherein the piezoelectric thread is thermally bound between the two elastic sheets.

9. The piezoelectric patch sensor of claim 2 wherein the two elastic sheets have an adhesive layer on the surface facing the piezoelectric thread for bonding the piezoelectric thread therebetween.

10. The piezoelectric patch sensor of claim 2 wherein each elastic sheet has a thickness of between 0.01 mm to 1 mm.

11. The piezoelectric patch sensor of claim 1 wherein the adhesive layer has a thickness of between 0.01 mm to 1 mm.

12. The piezoelectric patch sensor of claim 1 wherein the two conductive wires are connected at two ends of the piezoelectric thread.

13. The piezoelectric patch sensor of claim 1 wherein one of the two conductive wires is connected to the top of the piezoelectric thread and the other is connected to the bottom of the piezoelectric thread.

14. The piezoelectric patch sensor of claim 1 wherein the two conductive wires connected to the piezoelectric thread are electrically conductive paths formed using conductive glue.

15. The piezoelectric patch sensor of claim 1 wherein the two conductive wires connected to the piezoelectric thread are electrically conductive paths formed using printed conductive ink selected from the group consisting of silver, graphene, Carbone nanoparticles, Carbone nano tube, and PEDOT [poly(3,4-ethylenedioxythiophene) polystyrene sulfonate.

16. The piezoelectric patch sensor of claim 1 wherein the two conductive wires are deformable to withstand the deformation of muscle movement without exceeding mechanical constrain.

17. The piezoelectric patch sensor of claim 1 wherein the interface circuit comprises:
   a first unit connecting directly to the piezoelectric thread for converting the piezoelectric signal into a physical quantity;
   a second unit amplifying and filtering the piezoelectric signal; and
   a third unit recording and transmitting the piezoelectric signal to the host processor.

18. The piezoelectric patch sensor of claim 1 wherein the piezoelectric patch sensor is attached to the user indirectly via a wearable fabric that follows the movement of the muscle under the skin site.

19. The piezoelectric patch sensor of claim 1 wherein the attachment to the skin site is transversely or in an oblique angle with respect to the direction of muscle movement.

20. The piezoelectric patch sensor of claim 1 further comprising a grounded conductive layer that shields the piezoelectric thread against electromagnetic interference.

* * * * *